(12) United States Patent
Suen et al.

(10) Patent No.: US 8,334,242 B2
(45) Date of Patent: Dec. 18, 2012

(54) LUBRICATING COMPOSITION CONTAINING MULTIFUNCTIONAL BORATED HYDROXYLATED AMINE SALT OF A HINDERED PHENOLIC ACID

(75) Inventors: Yat Fan Suen, Pinole, CA (US); John Ward, San Francisco, CA (US); Trevor Miller, Dublin, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 52 days.

(21) Appl. No.: 12/902,760

(22) Filed: Oct. 12, 2010

(65) Prior Publication Data
US 2012/0088703 A1    Apr. 12, 2012

(51) Int. Cl.
C10M 139/00 (2006.01)
C10M 159/12 (2006.01)
C07C 59/00 (2006.01)

(52) U.S. Cl. ......... 508/194; 508/189; 508/516; 562/471
(58) Field of Classification Search .................. 508/194, 508/516; 562/471
See application file for complete search history.

(56) References Cited

U.S. PATENT DOCUMENTS

| | | | |
|---|---|---|---|
| 3,186,946 A | 6/1965 | Sluhan | |
| 3,227,739 A | 1/1966 | Versteeg | |
| 3,422,016 A * | 1/1969 | Cyba | 508/195 |
| 3,692,680 A | 9/1972 | Cyba | |
| 4,382,006 A | 5/1983 | Horodysky | |
| 4,426,305 A | 1/1984 | Malec | |
| 4,474,670 A | 10/1984 | Braid et al. | |
| 4,474,671 A | 10/1984 | Herd et al. | |
| 4,492,642 A | 1/1985 | Horodysky | |
| 4,549,975 A | 10/1985 | Horodysky | |
| RE32,295 E * | 11/1986 | Braid et al. | 508/195 |
| 4,622,158 A | 11/1986 | Walsh | |
| 4,892,670 A | 1/1990 | Mendelson | |
| 5,078,893 A | 1/1992 | Ryer et al. | |
| 5,308,518 A | 5/1994 | Habeeb et al. | |
| 5,320,768 A | 6/1994 | Gutierrez et al. | |
| 5,330,666 A | 7/1994 | Habeeb | |
| 5,698,498 A | 12/1997 | Luciani et al. | |
| 5,906,969 A | 5/1999 | Fyfe | |
| 7,691,794 B2 | 4/2010 | Muir | |
| 2007/0155631 A1 * | 7/2007 | Muir | 508/185 |
| 2008/0220170 A1 | 9/2008 | Van Der Flaas | |
| 2009/0094885 A1 * | 4/2009 | Muir | 44/300 |
| 2009/0099049 A1 * | 4/2009 | Muir | 508/189 |

FOREIGN PATENT DOCUMENTS

| | | |
|---|---|---|
| CA | 2648664 | 10/2007 |
| EP | 0314843 | 5/1989 |
| EP | 0157969 | 8/1992 |
| WO | WO8401169 | 3/1984 |
| WO | WO9321289 | 10/1993 |
| WO | WO9419434 | 9/1994 |

OTHER PUBLICATIONS

PCT International Search Report and Written Opinion International App. No. PCT/US2011/055430, Oct. 7, 2011.

* cited by examiner

Primary Examiner — Ellen McAvoy
Assistant Examiner — Vishal Vasisth
(74) Attorney, Agent, or Firm — Joseph P. Foley

(57) ABSTRACT

Multi-functional additives which impart improved antioxidancy to lubricating oil compositions and frictional properties resulting in improved fuel economy in an internal combustion engine are disclosed. More particularly disclosed is a boron containing salt of an oil soluble hydroxylated amine and a hindered phenolic acid product prepared by: a) reacting an oil soluble hydroxylated amine of the general formula II:

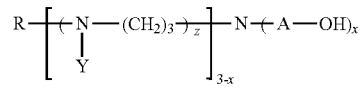

wherein A at each occurrence is each independently $C_2$-$C_6$ alkylene group; R is methyl or an alkyl or alkenyl group having $C_2$-$C_{24}$ carbon atoms; Y is hydrogen, $C_1$-$C_6$ alkyl group or A-OH; x is an integer of 1 or 2; and z is an integer of 0 or 1; with a boron containing compound under reactive conditions; and b) mixing the reaction product of step a) with a hindered phenolic acid.

15 Claims, No Drawings

LUBRICATING COMPOSITION CONTAINING MULTIFUNCTIONAL BORATED HYDROXYLATED AMINE SALT OF A HINDERED PHENOLIC ACID

FIELD OF INVENTION

Multi-functional additives which impart improved antioxidancy to lubricating oil compositions and frictional properties resulting in improved fuel economy in an internal combustion engine are disclosed. More particularly the multifunctional additive is a borated oil soluble hydroxylated amine salt of a hindered phenolic acid.

BACKGROUND

Improvements in fuel economy for heavy duty diesel engines have generally been achieved either through new engine design or through new approaches to lubricating oil formulating. Lubricant optimization is especially preferred over engine hardware changes due to its comparative lower cost per unit in fuel efficiency and possibility for backward compatibility with older engines. Organic friction modifiers, such as fatty acid esters, fatty acid amides, fatty amines, and the like, have been widely used in passenger car motor oils to reduce the energy losses due to friction in the various parts of the engine and to prevent engine wear thereby improving fuel economy. However, lubricating oil compositions containing these organic friction modifiers have not proven to be effective in diesel engines due to the different lubrications conditions found in diesel engines.

To improve fuel efficiency in heavy duty diesel engines, there has been a drive to develop new components which improve the frictional properties of the lubricating oil composition.

U.S. Pat. No. 828,733 discloses copper salts of hindered phenolic carboxylic acids.

U.S. Pat. No. 3,873,278 discloses an amine carboxylate salt derived from tall oil fatty acid and a $C_{12-18}$ alkyl or alkenyl amine containing about 3-7 oxyethylene groups which provide anti-stalling, anti-icing, anti-corrosion and detergent properties in motor fuels or gasoline.

U.S. Pat. No. 4,231,883 discloses the use of alkoxylated hydrocarbyl amine in a lubricating oil or fuel to reduce friction in an internal combustion engine. An example of the alkoxylated amine compounds that are disclosed is N,N-bis(2-hydroxyethyl)oleylamine.

U.S. Pat. No. 4,382,006 discloses a lubricating composition containing a friction reducing portion of a borated adduct of compounds which includes "Ethomeens". Borated salts of tertiary amines are disclosed as cutting fluids in U.S. Pat. No. 3,186,946.

WO 94/19434 discloses lubricating oil compositions containing alkoxylated amine salts of hydrocarbylsaliclic acids, hydrocarbylsulfonic acids, dihydrocarbyldithiophosphoric acids or dihydrocarbyldithiobenzoic acids trithiocyanuric acid which are stated to improve frictional properties. See also U.S. Pat. Nos. 5,330,666; 5,320,767; 5,320,766; and 5,308,518; respectively.

U.S. Pat. No. 5,078,893 discloses a lubricating composition adaptable for use as a power transmitting fluid having a lubricating oil, a friction modifying amount of a borated or unborated alkoxylated amine and an amount of organic phosphate ester effective to impart both antiwear and friction modification to the composition.

U.S. Pat. No. 7,691,764 discloses lubricating and fuel compositions containing metal free detergents prepared from the reaction product of an acidic organic compound, a boron compound and an amine. The acid organic compound exemplified is a hydrocarbyl salicylic acid.

SUMMARY

Disclosed is a multifunctional additive being a borated oil soluble hydroxylated amine salt of a hindered phenolic acid. The borated amine salt provides friction modifying properties and antioxidancy to lubricating oil compositions and suited for use lubricating oil compositions for internal combustion engines. Accordingly one aspect is directed to a boron containing salt of an oil soluble hydroxylated amine and a hindered phenolic acid product prepared by a) reacting an oil soluble hydroxylated amine of the general formula II:

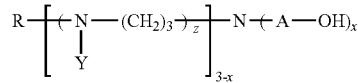

wherein

A at each occurrence is each independently $C_2$-$C_6$ alkylene group; R is methyl or an alkyl or alkenyl group having $C_2$-$C_{24}$ carbon atoms; Y is hydrogen, $C_1$-$C_6$ alkyl group or A-OH; x is an integer of 1 or 2; and z is an integer of 0 or 1; with a boron containing compound under reactive conditions; and b) mixing the reaction product of step a) with a hindered phenolic acid of the general formula

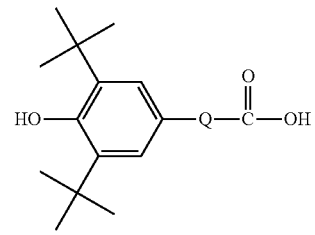

wherein Q is an alkylene group of 2 to 6 carbon atoms, to thereby form the boron containing salt of an oil soluble hydroxylated amine and a hindered phenolic acid.

Particularly suited hindered phenolic acids are selected wherein Q is selected from —$CH_2CH_2$—, —$CH_2CH(CH_3)$—, —$CH_2CH(CH_2CH_3)$—, —$CH_2CH(CH_2CH_2CH_3)$—, —$CH_2CH_2CH_2$—, and —$CH_2CH_2CH_2CH_2$—. Due to availability particularly suited are —$CH_2CH_2$—, —$CH_2CH(CH_3)$—, —$CH_2CH(CH_2CH_3)$—. In one aspect, the product prepared is directed to the salt wherein x is one, Y is independently selected from hydrogen or A-OH, and more particularly —$CH_2CH_2OH$ or —$CH_2CH(CH_3)OH$. Thus, in this aspect may further contain the proviso that when x is one, then z is zero.

In the soluble hydroxylated amine preferred R is an alkyl or alkenyl group having $C_6$ to $C_{24}$ carbon atoms and mixtures thereof, more particularly having $C_{12}$ to $C_{18}$ carbon atoms and mixtures thereof.

In other aspect, when x is 2 is directed to borated oil soluble hydroxylated amine wherein R is methyl, alkyl or alkenyl group having $C_2$-$C_{24}$ carbon atoms; Y is hydrogen, $C_1$-$C_6$ alkyl group or A-OH; and z is an integer of 0 or 1. With particularly suited A and Q being ethylene, propylene, —CH$_2$CH(CH$_3$)—, or —CH$_2$CH(CH$_2$CH$_3$)—. Preferred R groups having C$_6$-C$_{24}$ carbon atoms and more preferably C$_{12}$-C$_{18}$ alkyl or alkenyl groups. In one aspect z is zero. In another aspect z is one. In this regard, Y is hydrogen or A-OH with A being ethylene, propylene, —CH$_2$CH(CH$_3$)— and mixtures thereof.

The boron compound may be any boron containing compound capable of boronating the oil soluble hydroxylated amine represented by Formula II. Suitable boron compounds include boron trioxide or any of the various forms of boric acid including metaboric acid (HBO$_2$), orthoboric acid (H$_3$BO$_3$) and tetraboric acid (H$_2$B$_4$O$_7$). Alkyl borates such as the mono-, di- and tri-C$_{1-6}$ alkyl borates may employ. Particularly preferred is boric acid.

A further aspect is directed to formulated lubricating oil compositions, thus the oil of lubricating viscosity and minor amount of a borated oil soluble hydroxylated amine salt of a hindered phenolic acid may further contain other additives, suitable additives may include one or more of ashless dispersant, a metal detergent, an anti-wear additive, and an antioxidant.

Another aspect is directed to a method for reducing friction in an internal combustion engine which comprises operating the internal combustion engine with a lubricating oil composition containing an effective amount of the borated oil soluble hydroxylated amine salt of a hindered phenolic acid of having the general formula I. In this aspect, the amount of the borated oil soluble hydroxylated amine salt of a hindered phenolic acid is in amount from 0.05 wt % to about 5 wt % based upon the total weight percent of the lubricating oil composition. Particularly suited engines are diesel engines.

DETAILED DESCRIPTION

The 3,5,tertbutyl-4-hydroxyphenyl substituted acid employed herein is represented by the formula:

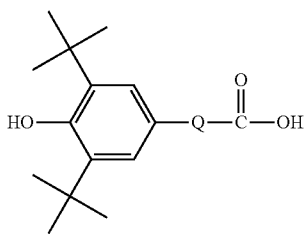

wherein Q is an alkylene group of 2 to 6 carbon atoms.

The alkylene group may be straight or branched chain, exemplarily including ethylene group, propylene group (1-methylethylene group, 2-methylethylene group), trimethylene group, butylene group (1-ethylethylene group, 2-ethylethylene group), 1,2-dimethylethylene group, 2,2-dimethylethylene group, 1-methyltrimethylene group, 2-methyltrimethylene group, 3-methyltrimethylene group, tetramethylene group, pentylene group, 1-ethyl-1-methylethylene group, 1-ethyl-2-methylethylene group, 1,1,2-trimethylethylene group, 1,2,2-trimethylethylene group, 1-ethyltrimethylene group, 2-ethyltrimethylene group, 3-ethyltrimethylene group, 1,1-dimethyltrimethylene group, 1,2-dimethyltrimethylene group, 1,3-dimethyltrimethylene group, 2,3-dimethyltrimethylene group, 3,3-dimethyltrimethylene group, 1-methyltetramethylene group, 2-methyltetramethylene group, 3-methyltetramethylene group, 4-methyltetramethylene group, pentamethylene group, hexylene group (1-butylethylene group, 2-butylethylene group), 1-methyl-1-propylethylene group, 1-methyl-2-propylethylene group, 2-methyl-2-propylethylene group, 1,1-diethylethylene group, 1,2-diethylethylene group, 2,2-diethylethylene group, 1-ethyl-1,2-dimethylethylene group, 1-ethyl-2,2-dimethylethylene group, 2-ethyl-1,1-dimethylethylene group, 2-ethyl-1,2-dimethylethylene group, 1,1,2,2-tetramethylethylene group, 1-propyltrimethylene group, 2-propyltrimethylene group, 3-propyltrimethylene group, 1-ethyl-1-methyltrimethylene group, 1-ethyl-2-methyltrimethylene group, 1-ethyl-3-methyltrimethylene group, 2-ethyl-1-methyltrimethylene group, 2-ethyl-2-methyltrimethylene group, 2-ethyl-3-methyltrimethylene group, 3-ethyl-1-methyltrimethylene group, 3-ethyl-2-methyltrimethylene group, 3-ethyl-3-methyltrimethylene group, 1,1,2-trimethyltrimethylene group, 1,1,3-trimethyltrimethylene group, 1,2,2-trimethyltrimethylene group, 1,2,3-trimethyltrimethylene group, 1,3,3-trimethyltrimethylene group, 2,2,3-trimethyltrimethylene group, 2,3,3-trimethyltrimethylene group, 1-ethyltetramethylene group, 2-ethyltetramethylene group, 3-ethyltetramethylene group, 4-ethyltetramethylene group, 1,1-dimethyltetramethylene group, 1,2-dimethyltetramethylene group, 1,3-dimethyltetramethylene group, 1,4-dimethyltetramethylene group, 2,2-dimethyltetramethylene group, 2,3-dimethyltetramethylene group, 2,4-dimethyltetramethylene group, 3,3-dimethyltetramethylene group, 3,4-dimethyltetramethylene group, 4,4-dimethyltetramethylene group, 1-methylpentamethylene group, 2-methylpentamethylene group, 3-methylpentamethylene group, 4-methylpentamethylene group, 5-methylpentamethylene group and hexamethylene group. Most preferred Q is 2-4 alkylene carbon atoms more preferably ethylene and methyl ethylene groups that may be made available with a minimum of reaction process steps and/or commercially available.

The 3,5-tertbutyl-4-hydroxyphenyl substituted acid can be prepared in various manners known in the art and commonly prepared by reacting a 2,6 alkylphenol with acrylic acid in the presence of a catalyst, (more typically with acrylic ester thereby hydrolyzed). Preferred substituted acids are 3-(3,5-Di-tert-butyl-4-hydroxy-phenyl)-propionic acid, 3-(3,5-Di-tert-butyl-4-hydroxy-phenyl)-2-methylpropionic acid, (3,5-Di-tert-butyl-4-hydroxy-phenyl)-butyric acid, 2-(3,5-Di-tert-butyl-4-hydroxy-benzyl)-butric acid, (3,5-Di-tert-butyl-4-hydroxy-phenyl)-pentanoic acid and (2,5-Di-tert-butyl-4-hydroxy-phenyl)-hexanoic acid. More particularly 3-(3,5-Di-tert-butyl-4-hydroxy-phenyl)-propionic acid, 3-(2,5-Di-tert-butyl-4-hydroxy-phenyl)-butyric acid, 3-(3,5-Di-tert-butyl-4-hydroxy-phenyl)-pentanoic acid and 3-(3,5-Di-tert-butyl-4-hydroxy-phenyl)-hexanoic acid. Even more preferred are 3-(3,5-Di-tert-butyl-4-hydroxy-phenyl)-propionic acid, 3-(3,5-Di-tert-butyl-4-hydroxy-phenyl)-2-methylpropionic acid, 2-(3,5-Di-tert-butyl-4-hydroxy-benzyl)-butric acid and 3-(3,5-Di-tert-butyl-4-hydroxy-phenyl)-butyric acid. And even more preferred are 3-(3,5-Di-tert-butyl-4-hydroxy-phenyl)-propionic acid and 3-(3,5-Di-tert-butyl-4-hydroxy-phenyl)-2-methylpropionic acid.

The oil soluble hydroxylated amine is represented by the formula:

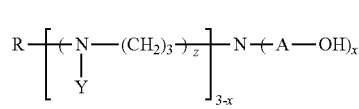

Formula II wherein A at each occurrence is each independently C$_2$-C$_6$ alkylene group; R is methyl or an alkyl or alkenyl group having $C_2$-$C_{24}$ carbon atoms; Y is hydrogen, $C_1$-$C_6$ alkyl group or A-OH; x is an integer of 1 or 2; and z is an integer of 0 or 1. Mixtures of the amines of the above formula may be used.

The A group, when employed more than occurrence in Formula II, can be the same or different but preferably is selected from ethylene, propylene, or butylene, and more preferably ethylene, 2-methylethylene or 2-ethylethylene. Typically A-OH is derived from an aliphatic epoxide, examples of useful epoxides include ethylene oxide, propylene oxide, 1,2-butene oxide and the like. Mixtures of epoxides may be employed. Y is preferably hydrogen or A-OH where A is described above.

The $C_1$-$C_{24}$ carbon atoms alkyl or $C_2$-$C_{24}$ carbon atoms alkenyl groups R may be of straight or branched chain: alkyl group exemplarily including methyl group, ethyl group, n-propyl group, isopropyl group, n-butyl group, isobutyl group, sec-butyl group, tert-butyl group, straight or branched pentyl group, straight or branched hexyl group, straight or branched heptyl group, straight or branched octyl group, straight or branched nonyl group, straight or branched decyl group, straight or branched undecyl group, straight or branched dodecyl group, straight or branched tridecyl group, straight or branched tetradecyl group, straight or branched pentadecyl group, straight or branched hexadecyl group, straight or branched heptadecyl group, straight or branched octadecyl group, straight or branched nonadecyl group, straight or branched eicosyl group, straight or branched heneicosyl group, straight or branched docosyl group, straight or branched tricosyl group, and straight or branched tetracosyl group; and alkenyl group exemplarily including vinyl group, propenyl group, isopropenyl group, straight or branched butenyl group, straight or branched pentenyl group, straight or branched hexenyl group, straight or branched heptenyl group, straight or branched octenyl group, straight or branched nonenyl group, straight or branched decenyl group, straight or branched undecenyl group, straight or branched dodecenyl group, straight or branched tridecenyl group, straight or branched tetradecenyl group, straight or branched pentadecenyl group, straight or branched hexadecenyl group, straight or branched heptadecenyl group, straight or branched octadecenyl group, straight or branched nonadecenyl group, straight or branched eicosenyl group, straight or branched heneicosenyl group, straight or branched docosenyl group, straight or branched tricosenyl group and straight or branched tetracosenyl group. In one aspect R may be a fatty alkyl or alkenyl group. By "fatty alkyl or alkyenyl" is meant an alkyl or alkenyl group which is derived from a natural fat or oil or from a derivative thereof such as the corresponding nitrile, by hydrogenation of the ester or nitrile group. Examples of fatty alkyl and alkenyl groups include myrystyl (tetradecyl), palmityl (hexadecyl), stearyl (octadecyl) and oleyl (9-octadecenyl).

In one aspect, when x is 1, wherein A, R, Y and z are defined hereabove, the oil soluble hydroxylated amine is represented by the formula:

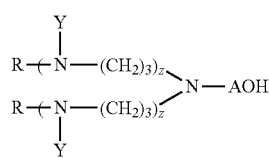

Formula III

In a more preferred aspect Y is independently selected from hydrogen or A-OH, and more particularly —$CH_2CH_2OH$ or —$CH_2CH(CH_3)OH$. In a particularly preferred aspect when x is one, z is one. Thus, in this aspect the oil soluble hydroxylated amine is represented by the formula I, above, with the variables defined above, further contains the proviso that when x is one, then z is zero. The resulting N,N dialkyl or dialkenyl hydroxyamines (R)(R)-N-AOH compounds are selected that R may be independently selected from methyl or alkyl or alkenyl group having $C_2$-$C_{24}$ carbon atoms, further defined herein above. More preferably R may be independently selected from $C_6$ to $C_{24}$ carbon atoms, and even more preferably independently selected from $C_8$ to $C_{18}$ carbon atoms. In one aspect, R is derived from the same moiety. Thus, particularly suited groups are 2-ethyl hexyl, $C_{12}$ groups and $C_{18}$ groups such as stearyl and oleic groups and mixtures thereof. Particularly preferred are the fatty alkyl or alkenyl groups selected from myrystyl (tetradecyl), palmityl (hexadecyl), stearyl (octadecyl) and oleyl (9-octadecenyl).

In another aspect, when x is 2, the oil soluble hydroxylated amine is represented by the formula:

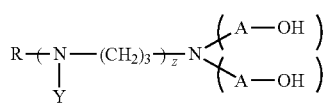

Formula IV wherein A at each occurrence is each independently $C_2$-$C_6$ alkylene group; R is an alkyl or alkenyl group having $C_1$-$C_{24}$ carbon atoms; Y is hydrogen, $C_1$-$C_6$ alkyl group or A-OH; and z is an integer of 0 or 1. Wherein the preferred groups are defined herein above.

In one aspect, the preferred groups are when z is zero: A can be the same or different but preferably is selected from ethylene, propylene, or butylene, and more preferably ethylene or 2-methylethylene or 2-ethylethylene; R is $C_6$-$C_{24}$ alkyl or alkenyl group and even more preferred to be a $C_8$-$C_{24}$ fatty alkyl and alkenyl groups defined above. Thus, particularly suited groups are 2-ethyl hexyl, $C_{12}$ groups and $C_{18}$ groups such as stearyl and oleic groups and mixtures thereof. Thus particularly preferred R groups are selected from the group consisting of tertradecyl, pentadecyl, hexadecyl octadecyl, eicosyl, tetradecenyl or octadecenyl groups. Useful oil soluble hydroxylated amines include "Ethomeens" a series of commercial mixtures available from AKZO NOBEL. Thus in one aspect when the amine is ethoyxlated and A are ethylene group and R is C12-C18. Suitable "Ethomeens" include "Ethomeen O/12", "Ethomeen 18/12", "Ethomeen S/12", "Ethomeen T/12", and "Ethomeen C/12": in these compounds A are both ethylene groups; and R is respectively oleyl, stearyl, a mixture of alkyl and alkenyl groups derived from soybean oil, a mixture of alkyl and alkenyl groups derived from tallow and a mixture of alkyl and alkenyl groups derived from coconut oil. In this aspect particularly suited compounds are selected from the group consisting of bis-(2-hydroxyethyl)cocoalkylamine, bis-(2-hydroxyethyl)oleylamine, bis-(2-hydroxyethyl)soyalkylamine, bis-(2-hydroxyethyl)tallowalkylamine, bis-(2-hydroxyethyl)dodecylamine and bis-(2-hydroxyethyl)octadecylamine. In another aspect when the amine is propylated and A are propylene groups and R is $C_{12-18}$ are commercially available as "Propomeen" from AKZO NOBEL such as "Propomeen O/12" and "Propomeen T/12" wherein the R group is derived from oleyl and derived from tallow. Particularly suited compounds are N-oleyl-1,1'-iminobis-2-propanol and N-tallowalkyl-1,1'-iminobis-2-propanol.

In another aspect, the preferred groups are when z is one: A can be the same or different but preferably is selected from ethylene, propylene, or butylene, and more preferably ethylene or 2-methylethylene or 2-ethylethylene; R is $C_8$-$C_{24}$ alkyl or alkenyl group and even more preferred to be fatty alkyl and alkenyl groups defined above. Thus particularly preferred R groups are selected from the group consisting of tetradecyl, pentadecyl, hexadecyl octadecyl, eicosyl, tetradecenyl or octadecenyl groups. And more preferably R is $C_{12-18}$. In one aspect Y is hydrogen, $C_1$-$C_6$ alkyl group or A-OH. More preferably Y is hydrogen or A-OH. Preferably A is ethylene and thus ethoxylated, however propylated compounds are also commercially available. "Ethoduomeen T-12" from AKZO NOBLE is Y is hydrogen and A is ethylene and R is derived from tallow; "Ethoduomeen T/13" and "Ethoduomeen T13/N" are where Y is -AOH, A is ethylene and R is derived from tallow.

The boron compound may be any boron containing compound capable of boronating the oil soluble hydroxylated amine represented by Formula II. Another aspect is boronating the oil soluble hydroxylated amine represented by Formula III. Yet another aspect is to boronating the oil soluble hydroxylated amine represented by Formula IV. Suitable boron compounds include boron trioxide or any of the various forms of boric acid including metaboric acid ($HBO_2$), orthoboric acid ($H_3BO_3$) and tetraboric acid ($H_2B_4O_2$). Alkyl borates such as the mono-, di- and tri-$C_{1-6}$ alkyl borates may employ. Thus suitable alkyl borates are the mono-, di- and tri-methylborates; the mono-, di- and tri-ethylborates; the mono-, di- and tri-propylborates, and the mono-, di- and tri-butylborates and mixtures thereof. The particularly preferred boron compound is boric acid and especially othoboric acid.

The oil soluble hydroxylated amine can be borated by adding the boron reactant (e.g. boric acid) to at least one of the oil soluble hydroxylated amine reactants represented by Formulae II, III or IV; in a suitable reaction vessel and heating the resulting reaction mixture to boronate the oil soluble hydroxylated amine. The reaction temperature is typically conducted at temperatures up to about 250° C., preferably from about 50° C. to about 225° C., and more preferably from about 75° C. to about 150° C. Time for the reaction can be from 2 to 4 hours up to 24 to 48 hours or more, depending upon the temperature, reaction pressure, solvents if used or catalyst if used. Typically the reaction is conducted under atmospheric pressure however the reaction may be conducted under pressure or vacuum. Furthermore, where conditions warrant it a solvent may be used. In general any relatively non-polar, unreactive solvent may be used, such as benzene, toluene, xylene and 1,4-dioxane or mineral oil. Other hydrocarbon and alcohol solvents and mixtures may also be employed. Generally the hydroxylated amine alone will serve as the solvent for the reaction mixture.

Typically the reaction is conducted until by-product water ceases to evolve from the reaction mixture indicating completion of the reaction. The removal of this water is facilitated by either by use of an inert gas, such as nitrogen contacting the surface of the reaction mixture or by conducting the reaction at reduced pressure. It is preferably that quantities of reactants of boron reactant to oil soluble hydroxylated amine is based upon nitrogen atoms on the oil soluble hydroxylated amine to atoms of boron or N:B equivalents form 0.3:1 to 1.5:1 and preferably about 0.5:1. Thus as depicted, boration can be complete or partial. Many borated amine complexes are known in the art see U.S. Pat. Nos. 4,474,671; 4,492,642; 4,622,158 and 4,892,670 and the like.

The borated oil soluble hydroxylated amine salt of a hindered phenolic acid is prepared by methods known to those skilled in the art. The borated oil soluble hydroxylated amine may be a mixture of components and its structure is difficult to depict. For illustrative purposes, a similar preparative reaction scheme of an oil soluble hydroxylated amine salt of a hindered phenolic acid is illustrated as follows:

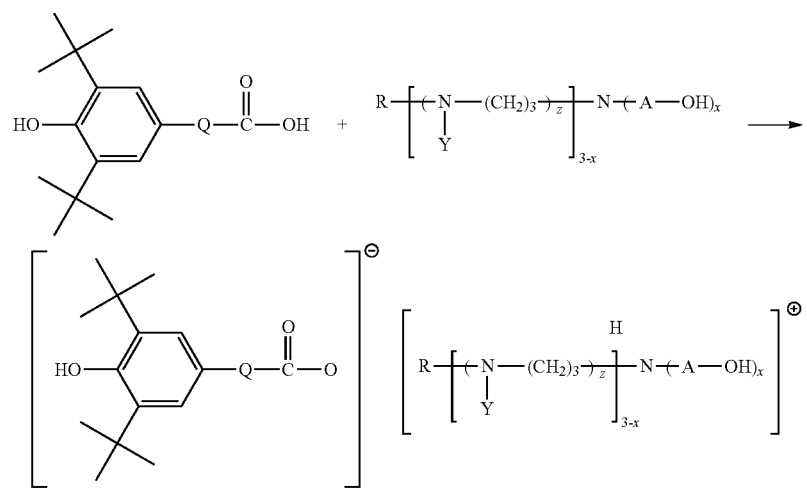

wherein
A, and Q each independently $C_2$-$C_6$ alkylene group; R is an alkyl or alkenyl group having $C_6$-$C_{24}$ carbon atoms; Y is hydrogen, $C_1$-$C_6$ alkyl group or A-OH; x is an integer of 1 or 2; and z is an integer of 0 or 1.

The amount of acid (A) hindered phenolic acid, or base (B) borated oil soluble hydroxylated amine, may be varied to achieve the desired acid/base balance of the final amine salt and determined by their acid and base values as well as the degree of boration. The equivalent ratio of A:B may be from 0.3:1 to 1.7:1. In one aspect, approximately equimolar amount of the borated hydroxylated amine and hindered phenolic acid are mixed together in an acid/base neutralization type reaction. Thus the equivalent ratio of A:B is 1:1-1.2. In one aspect, excess base is present. Typically, the borated oil soluble hydroxylated amine salt of a hindered phenolic acid are prepared by contacting (mixing and stirring) beginning at ambient or room temperature where the addition of one component may be slowed so the resultant exotherm does not carry the temperature above 100° C., preferably below 80° C., more preferably below 60° C.

The borated oil soluble hydroxylated amine salt of a hindered phenolic acid may advantageously be employed in a lubricating oil composition. The borated amine salt is a multifunctional additive in that when employed as an additive in lubricating oils, it provides reduced frictional characteristics and also imparts anti-oxidancy characteristics. It is also expected that the addition of boration to the oil soluble hydroxylated amine salt of a hindered phenolic acid will improve the seal compatibility of the salt. When employed in a lubricating oil composition it comprises a major amount of an oil of lubricating viscosity (major amount being greater than 50% by weight of the total composition, preferably more than 60%) and a minor amount of the borated oil soluble hydroxylated amine salt of a hindered phenolic acid. For finished lubricants, typically the amount of borated oil soluble hydroxylated amine salt of a hindered phenolic acid will be from about 0.001 wt % to about 10 wt % based upon the total composition. Preferably the borated oil soluble hydroxylated amine salt of a hindered phenolic acid is employed in a amount from 0.05 wt % to about 5 wt % and even more preferably from about 0.1 wt % to 1.5 wt % based upon the total weight of the lubricating oil composition.

The lubricating oil compositions of this invention can be used in the lubrication of essentially any internal composition engine, including automobile and truck engines, two cycle engines, diesel engines, aviation piston engines, marine and railroad engines and the like. Also contemplated are lubricating oils for gas fired engines, alcohol (e.g. methanol) powered engines, stationery powered engines, turbines and the like. Particularly useful are heavy duty diesel engines wherein said lubricating oil compositions of this invention can be employed to improve fuel economy and wherein the borated oil soluble hydroxylated amine salt of a hindered phenolic acid may provide an antioxidant benefit to the lubricating oil composition.

If desired, other additives known in the art may be added to the lubricating oil basestock. Such additives include dispersants, detergents, antiwear agents, extreme pressure agents, antioxidants, rust inhibitors, corrosion inhibitors, pour point depressants, viscosity index improvers, other friction modifiers and the like. Not limiting examples of such are herein below The oil of lubricating viscosity for use in the lubricating oil compositions of this invention, also referred to as a base oil, is typically present in a major amount, e.g., an amount of greater than 50 wt. %, preferably greater than about 70 wt. %, more preferably from about 80 to about 99.5 wt. % and most preferably from about 85 to about 98 wt. %, based on the total weight of the composition. The expression "base oil" as used herein shall be understood to mean a base stock or blend of base stocks which is a lubricant component that is produced by a single manufacturer to the same specifications (independent of feed source or manufacturer's location); that meets the same manufacturer's specification; and that is identified by a unique formula, product identification number, or both. The base oil for use herein can be any presently known or later-discovered base oil of lubricating viscosity used in formulating lubricating oil compositions for any and all such applications, e.g., engine oils, marine cylinder oils, functional fluids such as hydraulic oils, gear oils, transmission fluids, etc. Additionally, the base oils for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the base oil is dependent upon the application. Accordingly, the viscosity of a base oil for use herein will ordinarily range from about 2 to about 2000 centistokes (cSt) at 100° Centigrade (C). Generally, individually the base oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fischer-Tropsch process. For example, a suitable base oil is one that comprises little, if any, heavy fraction; e.g., little, if any, lube oil fraction of viscosity 20 cSt or higher at 100° C.

The base oil may be derived from natural lubricating oils, synthetic lubricating oils or mixtures thereof. Suitable base oil includes base stocks obtained by isomerization of synthetic wax and slack wax, as well as hydrocracked base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils includes, but is not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of 1,000, diphenyl ether of polyethylene glycol having a molecular weight of 500 to 1000, diethyl ether of polypropylene glycol having a molecular weight of 1,000 to 1,500, etc.) or mono- and polycarboxylic esters thereof such as, for example, the acetic esters, mixed $C_3$ to $C_8$ fatty acid esters, or the $C_{13}$ oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl)silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The ashless dispersant compounds employed in the lubricating oil composition of the present invention are generally used to maintain in suspension insoluble materials resulting from oxidation during use, thus preventing sludge flocculation and precipitation or deposition on metal parts. The lubricating oil composition of the present invention may contain one or more ashless dispersants. Nitrogen-containing ashless (metal-free) dispersants are basic, and contribute to the total base number or TBN (as can be measured by ASTM D2896) of a lubricating oil composition to which they are added, without introducing additional sulfated ash. The term "Total Base Number" or "TBN" as used herein refers to the amount of base equivalent to milligrams of KOH in one gram of sample. Thus, higher TBN numbers reflect more alkaline products, and therefore a greater alkalinity. TBN was determined using ASTM D 2896 test. An ashless dispersant generally comprises an oil soluble polymeric hydrocarbon backbone having functional groups that are capable of associating with particles to be dispersed. Many types of ashless dispersants are known in the art.

Representative examples of ashless dispersants include, but are not limited to, amines, alcohols, amides, or ester polar moieties attached to the polymer backbones via bridging groups. An ashless dispersant of the present invention may be, for example, selected from oil soluble salts, esters, aminoesters, amides, imides, and oxazolines of long chain hydrocarbon substituted mono and dicarboxylic acids or their anhydrides; thiocarboxylate derivatives of long chain hydrocarbons, long chain aliphatic hydrocarbons having a polyamine attached directly thereto; and Mannich condensation products formed by condensing a long chain substituted phenol with formaldehyde and polyalkylene polyamine.

Carboxylic dispersants are reaction products of carboxylic acylating agents (acids, anhydrides, esters, etc.) comprising at least about 34 and preferably at least about 54 carbon atoms with nitrogen containing compounds (such as amines), organic hydroxy compounds (such as aliphatic compounds including monohydric and polyhydric alcohols, or aromatic compounds including phenols and naphthols), and/or basic inorganic materials. These reaction products include imides, amides, and esters.

Succinimide dispersants are a type of carboxylic dispersants. They are produced by reacting hydrocarbyl-substituted succinic acylating agent with organic hydroxy compounds, or with amines comprising at least one hydrogen atom attached to a nitrogen atom, or with a mixture of the hydroxy compounds and amines. The term "succinic acylating agent" refers to a hydrocarbon-substituted succinic acid or a succinic acid-producing compound, the latter encompasses the acid itself. Such materials typically include hydrocarbyl-substituted succinic acids, anhydrides, esters (including half esters) and halides.

Succinic-based dispersants have a wide variety of chemical structures. One class of succinic-based dispersants is bissuccinimides having a hydrocarbyl group attached to the maleic moiety wherein each group is independently a hydrocarbyl group, such as a polyolefin-derived group. Typically the hydrocarbyl group is an alkyl group, such as a polyisobutyl group. Alternatively expressed, the hydrocarbyl groups can contain about 40 to about 500 carbon atoms, and these atoms may be present in aliphatic forms. The polyamines are alkylene polyamines wherein the alkylene group, commonly an ethylene ($C_2H_4$) group. Examples of succinimide dispersants include those described in, for example, U.S. Pat. Nos. 3,172,892, 4,234,435 and 6,165,235.

The polyalkenes from which the substituent groups are derived are typically homopolymers and interpolymers of polymerizable olefin monomers of 2 to about 16 carbon atoms, and usually 2 to 6 carbon atoms. The amines which are reacted with the succinic acylating agents to form the carboxylic dispersant composition can be monoamines or polyamines.

Certain fundamental types of succinimides and the related materials encompassed by the term of art "succinimide" are taught in U.S. Pat. Nos. 3,172,892; 3,219,666 and 3,272,746, the content of which is incorporated by reference herein. The term "succinimide" is understood in the art to include many of the amide, imide, and amidine species which may also be formed. The predominant product however is a succinimide and this term has been generally accepted as meaning the product of a reaction of an alkenyl substituted succinic acid or anhydride with a nitrogen-containing compound. Preferred succinimides, because of their commercial availability, are those succinimides prepared from a hydrocarbyl succinic anhydride, wherein the hydrocarbyl group contains from about 24 to about 350 carbon atoms, and an ethylene amine Examples of ethylene amines include ethylene diamine, diethylene triamine, triethylene tetramine, tetraethylene pentamine and the like. Particularly preferred are those succinimides prepared from polyisobutenyl succinic anhydride of about 70 to about 128 carbon atoms and tetraethylene pentamine or triethylene tetramine and mixtures thereof.

Succinimide dispersants are referred to as such since they normally contain nitrogen largely in the form of imide functionality, although the amide functionality may be in the form of amine salts, amides, imidazolines as well as mixtures thereof. To prepare a succinimide dispersant, one or more succinic acid-producing compounds and one or more amines are heated and typically water is removed, optionally in the presence of a substantially inert organic liquid solvent/diluent. The reaction temperature can range from about 80° C. up to the decomposition temperature of the mixture or the product, which typically falls between about 100° C. to about 300° C. Additional details and examples of procedures for preparing the succinimide dispersants of the present invention include those described in, for example, U.S. Pat. Nos. 3,172,892, 3,219,666, 3,272,746, 4,234,435, 6,165,235 and 6,440,905.

Suitable ashless dispersants may also include amine dispersants, which are reaction products of relatively high molecular weight aliphatic halides and amines, preferably polyalkylene polyamines Examples of such amine dispersants include those described in, for example, U.S. Pat. Nos. 3,275,554, 3,438,757, 3,454,555 and 3,565,804.

Suitable ashless dispersants may further include "Mannich dispersants," which are reaction products of alkyl phenols in which the alkyl group contains at least about 30 carbon atoms with aldehydes (especially formaldehyde) and amines (especially polyalkylene polyamines). Examples of such dispersants include those described in, for example, U.S. Pat. Nos. 3,036,003, 3,586,629. 3,591,598 and 3,980.569.

Suitable ashless dispersants may also be post-treated ashless dispersants such as post-treated succinimides, e.g., post-treatment processes involving borate or ethylene carbonate as disclosed in, for example, U.S. Pat. Nos. 4,612,132 and 4,746,446; and the like as well as other post-treatment processes. The carbonate-treated alkenyl succinimide is a polybutene succinimide derived from polybutenes having a molecular weight of about 450 to about 3000, preferably from about 900 to about 2500, more preferably from about 1300 to about 2300, and most preferably from about 2000 to about 2400, as well as mixtures of these molecular weights. Preferably, it is prepared by reacting, under reactive conditions, a mixture of a polybutene succinic acid derivative, an unsaturated acidic reagent copolymer of an unsaturated acidic reagent and an olefin, and a polyamine, such as disclosed in U.S. Pat. No. 5,716,912, the contents of which are incorporated herein by reference.

Suitable ashless dispersants may also be polymeric, which are interpolymers of oil-solubilizing monomers such as decyl methacrylate, vinyl decyl ether and high molecular weight olefins with monomers containing polar substitutes. Examples of polymeric dispersants include those described in, for example, U.S. Pat. Nos. 3,329,658; 3,449,250 and 3,666,730.

In a preferred embodiment of the present invention, an ashless dispersant for use in the lubricating oil composition is an ethylene, carbonate-treated bissuccinimide derived from a polyisobutenyl group having a number average molecular weight of about 2300. The dispersant(s) for use in the lubricating oil compositions of the present invention are preferably non-polymeric (e.g., are mono- or bissuccinimides).

Generally, the ashless dispersant is present in the lubricating oil composition in an amount ranging from about 3 to about 10 wt. %, and preferably from about 4 to about 8 wt. %, based on the total weight of the lubricating oil composition.

The at least one metal-containing detergent compound employed in the lubricating oil composition of the present invention functions both as a detergent to reduce or remove deposits and as an acid neutralizer or rust inhibitor, thereby reducing wear and corrosion and extending engine life. Detergents generally comprise a polar head with long hydrophobic tail, with the polar head comprising a metal salt of an acid organic compound.

The lubricating oil composition of the present invention may contain one or more detergents, which are normally salts, and especially overbased salts. Overbased salts, or overbased materials, are single phase, homogeneous Newtonian systems characterized by a metal content in excess of that which would be present according to the stoichiometry of the metal and the particular acidic organic compound reacted with the metal. The overbased materials are prepared by reacting an acidic material (typically an inorganic acid or lower carboxylic acid such as carbon dioxide) with a mixture comprising an acidic organic compound, in a reaction medium comprising at least one inert, organic solvent (such as mineral oil, naphtha, toluene, xylene) in the presence of a stoichiometric excess of a metal base and a promoter.

Useful acidic organic compounds for making the overbased compositions include carboxylic acids, sulfonic acids, phosphorus-containing acids, phenols and mixtures thereof. Preferably, the acidic organic compounds are carboxylic acids or sulfonic acids with sulfonic or thiousulfonic groups (such as hydrocarbyl-substituted benzenesulfonic acids), and hydrocarbyl-substituted salicylic acids.

Carboxylate detergents, e.g., salicylates, can be prepared by reacting an aromatic carboxylic acid with an appropriate metal compound such as an oxide or hydroxide. Neutral or overbased products may then be obtained by methods well known in the art. The aromatic moiety of the aromatic carboxylic acid can contain one or more heteroatoms such as nitrogen and oxygen. Preferably, the moiety contains only carbon atoms. More preferably, the moiety contains six or more carbon atoms, such as a benzene moiety. The aromatic carboxylic acid may contain one or more aromatic moieties, such as one or more benzene rings, optionally fused together or otherwise connected via alkylene bridges. Representative examples of aromatic carboxylic acids include salicylic acids and sulfurized derivatives thereof such as hydrocarbyl substituted salicylic acid and derivatives thereof. Processes for sulfurizing, for example, a hydrocarbyl-substituted salicylic acid, are known to those skilled in the art. Salicylic acids are typically prepared by carboxylation, for example, by the Kolbe-Schmitt process, of phenoxides. In that case, salicylic acids are generally obtained in a diluent in admixture with an uncarboxylated phenol.

Metal salts of phenols and sulfurized phenols are prepared by reaction with an appropriate metal compound such as an oxide or hydroxide. Neutral or overbased products may be obtained by methods well known in the art. For example, sulfurized phenols may be prepared by reacting a phenol with sulfur or a sulfur-containing compound such as hydrogen sulfide, sulfur monohalide or sulfur dihalide, to form products that are mixtures of compounds in which 2 or more phenols are bridged by sulfur-containing bridges.

The metal compounds useful in making the overbased salts are generally any Group I or Group II metal compounds in the Periodic Table of the Elements. Group I metals of the metal base include Group 1a alkali metals (e.g., sodium, potassium, lithium) as well as Group 1b metals such as copper. Group I metals are preferably sodium, potassium, lithium and copper, more preferably sodium or potassium, and particularly preferably sodium. Group II metals of the metal base include Group IIa alkaline earth metals (e.g., magnesium, calcium, strontium, barium) as well as Group IIb metals such as zinc or cadmium. Preferably, the Group II metals are magnesium, calcium, barium, or zinc, more preferably magnesium or calcium, and most preferably calcium.

Examples of the overbased detergents include, but are not limited to, calcium sulfonates, calcium phenates, calcium salicylates, calcium stearates and mixtures thereof. Overbased detergents suitable for use in the lubricating oil compositions of the present invention may be low overbased (e.g., an overbased detergent having a TBN below about 100). The TBN of such a low-overbased detergent may be from about 5 to about 50, or from about 10 to about 30, or from about 15 to about 20. Alternatively, the overbased detergents suitable for use in the lubricating oil compositions of the present invention may be high overbased (e.g., an overbased detergent having a TBN above about 100). The TBN of such a high-overbased detergent may be from about 150 to about 450, or from about 200 to about 350, or from about 250 to about 280.

A low-overbased calcium sulfonate detergent with a TBN of about 17 and a high-overbased sulfurized calcium phenate with a TBN of about 400 are two exemplary overbased detergents for use in the lubricating oil compositions of the present invention. The lubricating oil compositions of the present invention may contain more than one overbased detergent, which may be all low-TBN detergents, all high-TBN detergents, or a mixture thereof. For example, the lubricating oil compositions of the present invention may contain a first metal-containing detergent which is an overbased alkaline earth metal sulfonate detergent having a TBN of about 150 to about 450 and a second metal-containing detergent which is an overbased alkaline earth metal sulfonate detergent having a TBN of about 10 to about 50.

Suitable detergents for the lubricating oil compositions of the present invention also include "hybrid" detergents such as, for example, phenate/salicylates, sulfonate/phenates, sulfonate/salicylates, sulfonates/phenates/salicylates, and the like. Examples of hybrid detergents include those described in, for example, U.S. Pat. Nos. 6,153,565; 6,281,179; 6,429,178, and 6,429,179.

Generally, the metal-containing detergent is present in the lubricating oil composition in an amount ranging from about 0.25 to about 3 wt. %, and preferably from about 0.5 to about 2 wt. %, based on the total weight of the lubricating oil composition.

The antioxidant compounds employed in the lubricating oil composition of the present invention reduce the tendency of base stocks to deteriorate in service, which deterioration can be evidenced by the products of oxidation such as sludge and varnish-like deposits on the metal surfaces and by viscosity growth. Such oxidation inhibitors include hindered phenols, ashless oil soluble phenates and sulfurized phenates, alkyl-substituted diphenylamine, alkyl-substituted phenyl and naphthylamines and the like and mixtures thereof. Suitable diphenylamine antioxidants include, but are not limited to, monoalkylated diphenylamine, dialkylated diphenylamine, trialkylated diphenylamine, and the like and mixtures thereof. Representative examples of diphenylamine antioxidants include butyldiphenylamine, di-butyldiphenylamine, octyldiphenylamine, di-octyldiphenylamine, nonyldiphenylamine, di-nonyldiphenylamine, t-butyl-t-octyldiphenylamine, and the like and mixtures thereof.

Generally, the antioxidant compound is present in the lubricating oil composition in an amount ranging from about 0.2 to about 4 wt. %, and preferably from about 0.3 to about 1 wt. %, based on the total weight of the lubricating oil composition.

The anti-wear agent compounds employed in the lubricating oil composition of the present invention include molybdenum-containing complexes such as, for example, a molybdenum/nitrogen-containing complex. Such complexes are known in the art and are described, for example, in U.S. Pat. No. 4,263,152, the content of which is incorporated by reference herein.

Generally, the molybdenum/nitrogen-containing complex can be made with an organic solvent comprising a polar promoter during a complexation step and procedures for preparing such complexes are described, for example, e.g., in U.S. Pat. Nos. 4,259,194; 4,259,195; 4,261,843; 4,263,152; 4,265,773; 4,283,295; 4,285,822; 4,369,119; 4,370,246; 4,394,279; 4,402,840; and 6,962,896 and U.S. Patent Application Publication No. 2005/0209111, the contents of which are incorporated by reference herein. As shown in these references, the molybdenum/nitrogen-containing complex can further be sulfurized.

Generally, the anti-wear agent compounds are present in the lubricating oil composition in an amount ranging from about 0.25 to about 5 wt. %, and preferably from about 0.3 to about 2 wt. %, based on the total weight of the lubricating oil composition.

Preferably a minor amount of antiwear agent, a metal dihydrocarbyl dithiophosphate is added to the lubricant composition. The metal is preferably zinc. The dihydrocarbyldithiophosphate may be present in amount of 0.1 to 2.0 mass percent but typically low phosphorous compositions are desired so the dihydrocarbyldithiophosphate is employed at 0.25 to 1.2, preferably 0.5 to 0.7, mass %, in the lubricating oil composition. Preferably, zinc dialkylthiophosphate (ZDDP) is used. This provides antioxidant and antiwear properties to the lubricating composition. Such compounds may be prepared in accordance with known techniques by first forming a dithiophosphoric acid, usually by reaction of an alcohol or a phenol with $P_2S_5$ and then neutralizing the dithiophosphoric acid with a suitable zinc compound. Mixtures of alcohols may be used including mixtures of primary and secondary alcohols. Examples of such alcohols include, but are not restricted to the following list: iso-propanol, iso-octanol, 2-butanol, methyl isobutyl carbinol (4-methyl-1-pentane-2-ol), 1-pentanol, 2-methyl butanol, and 2-methyl-1-propanol. The hydrocarbyl groups can be a primary, secondary, or mixtures thereof, e.g. the compounds may contains primary and/or secondary alkyl groups derived from primary or secondary carbon atoms. Moreover, when employed, there is preferably at least 50, more preferably 75 or more, most preferably 85 to 100, mass % secondary alkyl groups; an example is a ZDDP having 85 mass % secondary alkyl groups and 15 mass % primary alkyl groups, such as a ZDDP made from 85 mass % butan-2-ol and 15 mass % iso-octanol. Even more preferred is a ZDDP derived from derived from sec-butanol and methylisobutylcarbinol and most preferably wherein the sec-butanol is 75 mole percent.

The metal dihydrocarbyldithiophosphate provides most if not all, of the phosphorus content of the lubricating oil composition. Amounts are present in the lubricating oil composition to provide a phosphorus content, expressed as mass % elemental phosphorus, of 0.10 or less, preferably 0.08 or less, and more preferably 0.075 or less, such as in the range of 0.025 to 0.07.

The lubricating oil compositions of the present invention can be conveniently prepared by simply blending or mixing the lubricating oil and the borated oil soluble hydroxylated amine salt of a hindered phenolic acid, optionally other additives may be blended such as the ashless dispersant, at least one metal-containing detergent, antioxidant and anti-wear agent, optionally with other additives, with the oil of lubricating viscosity. The borated oil soluble hydroxylated amine salt of a hindered phenolic acid, ashless dispersant, metal-containing detergent, antioxidant and anti-wear agent may also be preblended as a concentrate or package with various other additives, if desired, in the appropriate ratios to facilitate blending of a lubricating composition containing the desired concentration of additives. The borated oil soluble hydroxylated amine salt of a hindered phenolic acid, ashless dispersant, at least one metal-containing detergent, antioxidant and anti-wear agent are blended with the base oil using a concentration at which they provide improved friction effect and are both soluble in the oil and compatible with other additives in the desired finished lubricating oil. Compatibility in this instance generally means that the present compounds as well as being oil soluble in the applicable treat rate also do not cause other additives to precipitate under normal conditions. Suitable oil solubility/compatibility ranges for a given compound of lubricating oil formulation can be determined by those having ordinary skill in the art using routine solubility testing procedures. For example, precipitation from a formulated lubricating oil composition at ambient conditions (about 20° C. to 25° C.) can be measured by either actual precipitation from the oil composition or the formulation of a "cloudy" solution which evidences formation of insoluble wax particles.

The lubricating oil compositions of the present invention may also contain other conventional additives for imparting auxiliary functions to give a finished lubricating oil composition in which these additives are dispersed or dissolved. For example, the lubricating oil compositions can be blended with friction modifiers, rust inhibitors, dehazing agents, demulsifying agents, metal deactivating agents, pour point depressants, antifoaming agents, co-solvents, package compatibilisers, corrosion-inhibitors, dyes, extreme pressure agents and the like and mixtures thereof. A variety of the additives are known and commercially available. These additives, or their analogous compounds, can be employed for the preparation of the lubricating oil compositions of the invention by the usual blending procedures.

Examples of supplemental friction modifiers include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are incorporated by reference herein; friction modifiers obtained from a reaction product of a $C_4$ to $C_{25}$, preferably a $C_6$ to $C_{24}$, and most preferably a $C_6$ to $C_{20}$, fatty acid ester and a nitrogen-containing compound selected from the group consisting of ammonia, and an alkanolamine and the like and mixtures thereof. The friction modifier can be incorporated in the lubricating oil composition in an amount ranging of from about 0.02 to about 2.0 wt. % of the lubricating oil composition, preferably from about 0.05 to about 1.0 wt. %, and more preferably from about 0.1 to about 0.5 wt. %.

Examples of rust inhibitors include, but are not limited to, nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; metal soaps; fatty acid amine salts; metal salts of heavy sulfonic acid; partial carboxylic acid ester of polyhydric alcohol; phosphoric esters; (short-chain) alkenyl succinic acids; partial esters thereof and nitrogen-containing derivatives thereof; synthetic alkarylsulfonates, e.g., metal dinonylnaphthalene sulfonates; and the like and mixtures thereof.

Examples of antifoaming agents include, but are not limited to, polymers of alkyl methacrylate; polymers of dimethylsilicone and the like and mixtures thereof.

The lubricating composition of the present invention may also contain a viscosity index improver. Examples of the viscosity index improvers include poly-(alkyl methacrylate), ethylene-propylene copolymer, styrene-butadiene copolymer, and polyisoprene. Viscosity index improvers of the dispersant type (having increased dispersancy) or multifunction type are also employed. These viscosity index improvers can be used singly or in combination. The amount of viscosity index improver to be incorporated into an engine oil varies with desired viscosity of the compounded engine oil, and generally in the range of about 0.5 to about 20 wt. % per total amount of the engine oil.

EXAMPLES

The invention is further illustrated by the following examples which are not to be considered as limitative of its scope.

Example 1

Salt of Borated 2,2'-((2-ethylhexyl)azanediyl)diethanol and 3,5-di-tert-butyl-4-hydroxyphenylpropionic acid Preparation of Borated 2,2'-((2-ethylhexyl)azanediyl)diethanol 2-Ethyl-1-hexanol (1 mol. equiv.) was dissolved in tetrahydrofuran at a 2M concentration. To this solution was added $CBr_4$ (1.25 mol. equiv.). The solution was cooled to 0° C. and triphenylphosphine (1.25 mol. equiv) was added slowly. The solution was allowed to stir for approximately 20 minutes. Water was added and the product extracted three times with dichloromethane. The organic extracts were collected, dried over $Na_2SO_4$, filtered, and concentrated under vacuum to afford 3-(bromomethyl)hexane.

3-(Bromomethyl)hexane (1 mol. equiv.) was dissolved in acetonitrile at a 2M concentration. To this solution was added diethanolamine (3 mol. equiv.), $K_2CO_3$ (2.5 mol. equiv.) and catalytic KI (0.025 mol. equiv.). The flask was fitted with a water cooled reflux condenser and the solution was refluxed for 18 hours. The solution was subsequently cooled to room temperature and filtered. Acetonitrile was removed under vacuum. The crude product was dissolved in ethyl acetate and washed with water and brine. The organic extract was collected, dried over $Na_2SO_4$, filtered and concentrated under vacuum to afford the product.

The 2,2'-((2-Ethylhexyl)azanediyl)diethanol (1 mol. equiv.), as prepared above, was dissolved in toluene at a 1M concentration. To this solution was added boric acid (1 mol. Equiv.) The flask was fitted with a water coiled reflux condenser and the solution was refluxed for 18 hours. The solution was cooled and concentrated under vacuum to eliminate toluene and water. One mol. equivalent of the borated 2,2'-(2-Ethylhexyl)azanediyl)diethanol (1 mol. equiv.), prepared above was dissolved in dichloromethane at a 1M concentration. To this solution was added 3,5-di-tert-butyl-4-hydroxyphenylpropionic acid (1 mol. equiv.), available commercially from Alfa Aesar. After 18 hours, the dichloromethane was removed under vacuum to afford the salt.

Example 2

Salt of Borated bis(2-hydroxyethyl)dodecylamine and 3,5-di-tert-butyl-4-hydroxyphenylpropionic acid Bis(2-hydroxyethyl)dodecylamine (1 mol. equiv.), was prepared according to the procedure described in Example 1 except that 1-dodecanol was used rather than 2-ethyl-1-hexanol. The Bis(2-hydroxyethyl)dodecylamine was dissolved in toluene at a 1M concentration to which was added boric acid (1 mol. equiv.). The reaction flask was fitting with a water coiled reflux condenser and the solution was refluxed for 18 hours. The solution was cooled and concentrated under vacuum to eliminate toluene and water.

The borated bis(2-hydroxyethyl)dodecylamine was dissolved in dichloromethane at a 1M concentration. To this solution was added 3,5-di-tert-butyl-4-hydroxyphenylpropionic acid (1 mol. equiv.). After 18 hours, the dichloromethane was removed under vacuum to afford the salt.

Example 3

Salt of Borated bis(2-hydroxyethyl)oleylamine and 3,5-di-tert-butyl-4-hydroxyphenylpropionic acid Bis(2-hydroxyethyl)oleylamine (1 mol. equiv.) was dissolved in toluene at a 1M concentration. Bis(2-hydroxyethyl) oleylamine was available commercially from AZKO NOBEL as "ETHOMEEN O/12". To this solution was added boric acid (1 mol. equiv.). The flask was fitted with a water coiled reflux condenser and the solution was refluxed for 18 hours. The solution was cooled and concentrated under vacuum to eliminate toluene and water. One mol. equiv. of the borated bis(2-hydroxyethyl)oleylamine compound was dissolved in dichloromethane at a 1M concentration. To this solution was added 3,5-di-tert-butyl-4-hydroxyphenylpropionic acid (1 mol. equiv.). After 18 hours, the dichloromethane was removed under vacuum to afford the salt.

Example 4 (Comparative)

Boron Source with 3,5-di-tert-butyl-4-hydroxyphenylpropionic acid 5-di-tert-butyl-4-hydroxyphenylpropionic acid (1 mol. equiv.) was dissolved in toluene at 1M concentration. To this solution was added boric acid (3 mol. equiv.). The flask was fitted with a water coiled reflux condenser and the solution was refluxed for 18 hours. The solution was cooled and concentrated under vacuum to eliminate toluene. The resulting solution was analyzed by IR and NMR spectra which indicated there was no chemical reaction and the reactants were the starting materials. In the NMR, the OH peak of the 5-di-tert-butyl-4-hydroxyphenylpropionic acid was clearly evident; from IR spectra, the broad acid peak was also present. In conclusion there was no chemical reaction and the solution merely contained a physical mixture of 5-di-tert-butyl-4-hydroxyphenylpropionic acid and boric acid.

Evaluation of Friction Performance

Performance Example A—Baseline A

A 5W-30 oils (SAE viscosity grade) baseline lubricating oil composition was prepared using the following additives: approximately 10 wt % of a mixture polyalkylsucciniminde which optionally a portion have been post-treated, a mixture of low overbased and high overbased calcium and magnesium sulfonates, a borated calcium sulfonate, a high overbased calcium phenate, zinc dialkyldithiophosphate, an antioxidant including 0.5 wt. % of a hindered phenolic ester and 0.3 wt. % of a diphenylamine a viscosity index improver, a pour point depressant and a foam inhibitor to a majority of a Group II baseoil.

Performance Example B (Comparative)

A lubricating oil composition was prepared by top-treating the baseline formulation of Performance Example A with 1 wt. % of a borated glycerol monooleate as disclosed in U.S. Pat. No. 5,629,272.

Additional lubricating oil compositions were also prepared by top-treating the baseline formulation of Example A with 1 wt. % of one salt as prepared in Examples 1-3. The lubricating oil compositions presented in the examples were 5W-30 oils (SAE viscosity grade).

The compositions described above were tested for friction performance in a Mini-Traction Machine (MTM) bench test. The MTM is manufactured by PCS Instruments and operates with a ball (0.75 inches 8620 steel ball) loaded against a rotating disk (52100 steel). The conditions employ a load of approximately 10-30 Newtons, a speed of approximately 10-2000 mm/s and a temperature of approximately 125-150° C. In this bench test, friction performance is measured as the comparison of the total area under the second Stribeck curve generated with the baseline formulation and the second Stribeck curve generated with the baseline formulation top-treated with a friction modifier. Lower total area values correspond to better friction performance of the oil.

TABLE 1

Frictional properties

| Performance Example | Friction Modifier | Stribeck Area |
|---|---|---|
| Performance Ex. A | None | 128 |
| Performance Ex. B | Borated glycerol monooleate | 140 |
| Performance Ex. 1 | Salt of borated 2,2'-((2-ethylhexyl)azanediyl)diethanol and 3,5-Di-tert-butyl-4-hydroxyphenylpropionic acid | 123 |
| Performance Ex. 2 | Salt of borated bis(2-hydroxyethyl)dodecylamine and 3,5-Di-tert-butyl-4-hydroxyphenylpropionic acid | 124 |
| Performance Ex. 3 | Salt of borated bis(2-hydroxyethyl)oleylamine and 3,5-Di-tert-butyl-4-hydroxyphenylpropionic acid | 84 |

The results demonstrate that lubricating oil compositions of the present invention demonstrate superior friction performance to lubricating oil compositions over base line as well as those containing a commonly employed borated glycerol monooleate friction modifier.

What is claimed is:

1. A boron containing salt of an oil soluble hydroxylated amine and a hindered phenolic acid product prepared by:
   a) reacting an oil soluble hydroxylated amine of the general formula II:

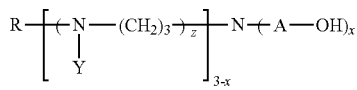

wherein
   A at each occurrence is each independently $C_2$-$C_6$ alkylene group; R is methyl or an alkyl or alkenyl group having $C_2$-$C_{24}$ carbon atoms; Y is hydrogen, $C_1$-$C_6$ alkyl group or A-OH; x is an integer of 1 or 2; and z is an integer of 1; with a boron containing compound under reactive conditions; and
   b) mixing the reaction product of step a) with a hindered phenolic acid of the general formula

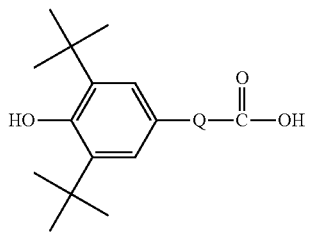

wherein Q is an alkylene group of 2 to 6 carbon atoms, to thereby form the boron containing salt of an oil soluble hydroxylated amine and a hindered phenolic acid.

2. The product prepared by claim 1 wherein Q is selected from —$CH_2CH_2$—, —$CH_2CH(CH_3)$—, —$CH_2CH(CH_2CH_3)$—, —$CH_2CH(CH_2CH_2CH_3)$—, —$CH_2CH_2CH_2$—, and —$CH_2CH_2CH_2CH_2$—.

3. The product prepared by claim 1 wherein x is one.

4. The product prepared by claim 3 wherein Y is hydrogen or -AOH.

5. The product prepared by claim 4 wherein A is selected from the group consisting of ethylene, propylene and mixtures thereof.

6. The product prepared by claim 1 wherein R is an alkyl or alkenyl group having $C_6$ to $C_{24}$ carbon atoms and mixtures thereof.

7. The product prepared by claim 6 wherein R is an alkyl or alkenyl group having $C_{12}$ to $C_{18}$ carbon atoms and mixtures thereof.

8. The product prepared by claim 1 wherein x is two.

9. The product prepared by claim 8 wherein Y is hydrogen or -AOH.

10. The product prepared by claim 8 wherein R is an alkyl or alkenyl group having $C_6$ to $C_{24}$ carbon atoms and mixtures thereof.

11. The product prepared by claim 1 wherein the boron containing compound is boric acid.

12. A lubricating oil composition comprising an oil of lubricating viscosity and the product prepared by claim 1.

13. A method for reducing friction in an internal combustion engine which comprises operating the internal combustion engine with a lubricating oil composition containing an effective amount of product prepared by claim 1.

14. The method of claim 13, wherein the amount of product prepared by claim 1 is in amount from 0.05 wt % to about 5 wt % based upon the total weight percent of the lubricating oil composition.

15. The method of claim 14, wherein the internal combustion engine is a diesel engine.

* * * * *